US009002285B2

(12) United States Patent
Hasegawa et al.

(10) Patent No.: US 9,002,285 B2
(45) Date of Patent: Apr. 7, 2015

(54) PORTABLE WIRELESS TERMINAL, WIRELESS TERMINAL, WIRELESS COMMUNICATION SYSTEM, AND WIRELESS COMMUNICATION METHOD

(75) Inventors: Yasuhiro Hasegawa, Tokyo (JP); Manabu Ishizeki, Tokyo (JP)

(73) Assignee: Olympus Corporation, Tokyo (JP)

( * ) Notice: Subject to any disclaimer, the term of this patent is extended or adjusted under 35 U.S.C. 154(b) by 165 days.

(21) Appl. No.: 13/448,972

(22) Filed: Apr. 17, 2012

(65) Prior Publication Data

US 2012/0202433 A1 Aug. 9, 2012

Related U.S. Application Data

(63) Continuation of application No. PCT/JP2010/066786, filed on Sep. 28, 2010.

(30) Foreign Application Priority Data

Oct. 23, 2009 (JP) ................................. 2009-244353

(51) Int. Cl.
*H04B 7/00* (2006.01)
*A61B 1/04* (2006.01)
*A61B 1/00* (2006.01)
*H04W 72/02* (2009.01)

(52) U.S. Cl.
CPC .............. *A61B 1/04* (2013.01); *A61B 1/00016* (2013.01); *A61B 1/00059* (2013.01); *H04W 72/02* (2013.01)

(58) Field of Classification Search
CPC ................................ G08G 5/0013; H03J 7/02
USPC .................................................. 455/66.1, 71
See application file for complete search history.

(56) References Cited

U.S. PATENT DOCUMENTS 6,167,260 A * 12/2000 Azam et al. .................... 455/434
8,358,981 B1 * 1/2013 Gitlin et al. .................. 455/66.1
(Continued)

FOREIGN PATENT DOCUMENTS

CN 101242778 A 8/2008
EP 1 707 106 A2 10/2006
(Continued)

OTHER PUBLICATIONS

Extended European Search Report dated Sep. 26, 2012, issued in corresponding European Patent Application No. 10824763.6 (12 pages).
(Continued)

*Primary Examiner* — Hai V Nguyen
(74) *Attorney, Agent, or Firm* — Westerman, Hattori, Daniels & Adrian, LLP

(57) ABSTRACT

Disclosed is a wireless terminal for performing independent distributed-type wireless communication with a portable wireless terminal. The wireless terminal is provided with: a channel setting section for setting a channel on which wireless communication with the portable wireless terminal is performed; a trigger receiving section for receiving a trigger; a free channel search section for searching for a free channel in response to the trigger received, and for delivering a signal, which changes the set channel in accordance with the search result, to the channel setting section; and a transmission section for transmitting to the portable wireless terminal a signal which reports the change.

5 Claims, 9 Drawing Sheets

(56) References Cited

U.S. PATENT DOCUMENTS

| | | | |
|---|---|---|---|
| 8,406,490 B2* | 3/2013 | Gat et al. | 382/128 |
| 8,858,432 B2* | 10/2014 | Robertson et al. | 600/300 |
| 2006/0155174 A1* | 7/2006 | Glukhovsky et al. | 600/301 |
| 2006/0193505 A1* | 8/2006 | Glukhovsky et al. | 382/128 |
| 2006/0217591 A1* | 9/2006 | Abe | 600/118 |
| 2006/0217593 A1* | 9/2006 | Gilad et al. | 600/160 |
| 2007/0140424 A1 | 6/2007 | Serceki | |
| 2008/0051633 A1* | 2/2008 | Blijevsky | 600/117 |
| 2008/0114225 A1* | 5/2008 | Rabinovitz | 600/310 |
| 2008/0146896 A1* | 6/2008 | Rabinowitz et al. | 600/309 |
| 2008/0167523 A1* | 7/2008 | Uchiyama et al. | 600/114 |
| 2008/0208077 A1* | 8/2008 | Iddan et al. | 600/582 |
| 2008/0227394 A1* | 9/2008 | Homan et al. | 455/41.3 |
| 2008/0294023 A1* | 11/2008 | Rabinovitz et al. | 600/309 |
| 2009/0002177 A1 | 1/2009 | Kimoto et al. | |
| 2009/0023992 A1* | 1/2009 | Gilad et al. | 600/109 |
| 2009/0131784 A1* | 5/2009 | Betesh | 600/424 |
| 2009/0202117 A1* | 8/2009 | Vilarino et al. | 382/128 |
| 2009/0214111 A1* | 8/2009 | Zinaty et al. | 382/167 |
| 2009/0303319 A1* | 12/2009 | Sato et al. | 348/65 |
| 2009/0318766 A1* | 12/2009 | Rabinovitz et al. | 600/160 |
| 2010/0014463 A1 | 1/2010 | Nagai et al. | |
| 2010/0032546 A1* | 2/2010 | Kawano et al. | 250/205 |
| 2010/0119133 A1* | 5/2010 | Glukhovsky et al. | 382/128 |
| 2010/0322866 A1* | 12/2010 | Rabinovitz | 424/9.6 |
| 2011/0243116 A1* | 10/2011 | Endo et al. | 370/338 |
| 2011/0257481 A1* | 10/2011 | Ogawa et al. | 600/109 |
| 2012/0062715 A1* | 3/2012 | Endo et al. | 348/65 |
| 2012/0200688 A1* | 8/2012 | Endo et al. | 348/74 |
| 2012/0238812 A1* | 9/2012 | Blijevsky | 600/109 |
| 2013/0137377 A1* | 5/2013 | Endo et al. | 455/66.1 |
| 2014/0163316 A1* | 6/2014 | Koide | 600/103 |

FOREIGN PATENT DOCUMENTS

| | | |
|---|---|---|
| EP | 1 927 314 A1 | 6/2008 |
| JP | 54-11607 A | 1/1979 |
| JP | 10-94047 A | 4/1998 |
| JP | 2003-265402 A | 9/2003 |
| JP | 2005-006082 A | 1/2005 |
| JP | 2006-509574 A | 3/2006 |
| JP | 2006-271432 A | 10/2006 |
| JP | 2007-167649 A | 7/2007 |
| WO | 2004/054430 A2 | 7/2004 |
| WO | 2008/069245 A1 | 6/2008 |

OTHER PUBLICATIONS

International Search Report of PCT/JP2010/066786, mailing date of Nov. 22, 2010.

Japanese Office Action dated Feb. 4, 2014, issued in Japanese Patent Application No. 2009-244353, w/English translation (7 pages).

Office Action dated Jan. 15, 2015, issued in corresponding Chinese Patent Application No. 201080046671.1, with English Translation (23 pages).

\* cited by examiner

PORTABLE WIRELESS TERMINAL, WIRELESS TERMINAL, WIRELESS COMMUNICATION SYSTEM, AND WIRELESS COMMUNICATION METHOD

CROSS REFERENCE TO RELATED APPLICATIONS

This application is a continuation application based on a PCT Patent Application No. PCT/JP2010/066786, filed Sep. 28, 2010, whose priority is claimed on Japanese Patent Application No. 2009-244353, filed on Oct. 23, 2009, the entire content of which are hereby incorporated by reference.

BACKGROUND OF THE INVENTION

1. Field of the Invention

The present invention relates to a portable wireless terminal, a wireless terminal, a wireless communication system, and a wireless communication method.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

Conventionally, medical diagnosis using an endoscope in the medical field has been performed. An image capturing element such as a charge coupled device (CCD) is embedded in the head of an insertion part of an endoscope scope (hereinafter referred to as a scope), and a processor performs signal processing with respect to an image capturing signal photographed by the CCD, so that it is possible to observe an image (an endoscope image) of an inside of a body through a monitor. Normally, the scope and the processor are connected to each other using a signal cable.

Meanwhile, a wireless endoscope system in which the scope and the processor are connected to each other in a wireless manner has been proposed. In the wireless endoscope system, a limitation of an operation using a signal cable is reduced, resulting in the improvement of operability. Furthermore, in an electronic endoscope system in which the scope and the processor are connected to each other using a signal cable, it is necessary to isolate the scope from the processor in order to ensure stability. However, in the wireless endoscope system, since a wireless connection is established instead of an electrical connection, a configuration for the isolation is not necessary. However, in the wireless endoscope system, in order to perform reliable data communication between the processor and a plurality of wireless endoscopes or between the processor and other wireless communication devices, it is necessary to consider interference caused by wireless communication.

As a countermeasure thereto, in general, an autonomous distributed wireless terminal checks a peripheral radio wave state before starting communication, selects a channel less affected by interference, and starts communication. For example, an electronic endoscope system has been known in which a processor regularly receives a report of a channel used from a scope operating nearby, stores information on the channel used, automatically assigns an unused channel when a channel assignment request signal has been received from a target scope, and uses the unused channel as a channel for the scope (for example, refer to Japanese Unexamined Patent Application, First Publication, No. 2006-271432, which will be referred to as patent document 1).

In the technology disclosed in patent document 1, after a channel to be used for image transmission between the processor and the scope is set, it is not possible to change the channel. Therefore, after the channel to be used for image transmission is set once, even when a communication state of the channel set based on a peripheral radio wave condition and the like is deteriorated, communication should be continued through the channel.

The present invention provides a portable wireless terminal, a wireless terminal, a wireless communication system, and a wireless communication method, by which, even after a channel to be used for communication between wireless terminals is set, it is possible to change the channel to be used for communication between the wireless terminals.

SUMMARY

A wireless terminal performs autonomous distributed wireless communication with a portable wireless terminal. The wireless terminal includes: a channel setting unit that sets a channel to be used for wireless communication with the portable wireless terminal; a trigger receiver unit that receives a trigger; a vacant channel search unit that searches for a vacant channel according to the received trigger and sends a signal for changing the set channel to the channel setting unit based on a search result; and a transmitter unit that transmits a signal for reporting the changing to the portable wireless terminal.

The channel setting unit may set the channel before a signal sent from the portable wireless terminal is received.

While the wireless communication with the portable wireless terminal is being performed using the channel, the vacant channel search unit may send the signal for changing the channel to the channel setting unit.

The trigger receiver unit may receive the trigger from the portable wireless terminal.

The wireless terminal may be a processor device of a wireless endoscope system.

A portable wireless terminal performs autonomous distributed wireless communication with a wireless terminal. The wireless terminal includes a channel setting unit that sets a channel to be used for wireless communication with the portable wireless terminal, a trigger receiver unit that receives a trigger, a vacant channel search unit that searches for a vacant channel according to the received trigger and sends a signal for changing the set channel to the channel setting unit based on a search result, and a transmitter unit that transmits a signal for reporting the change to the portable wireless terminal. The portable wireless terminal includes: a sending unit that sends a trigger to the wireless terminal, the trigger being used for allowing the wireless terminal to search for a vacant channel.

The sending unit may send the trigger when the wireless communication with the wireless terminal is started.

The sending unit may send the trigger while the wireless communication with the wireless terminal is being performed.

The portable wireless terminal may be an endoscope scope of a wireless endoscope system.

A wireless communication system in which a portable wireless terminal and a wireless terminal perform autonomous distributed wireless communication, wherein the portable wireless terminal includes: a sending unit that sends a trigger to the wireless terminal, the trigger being used for allowing the wireless terminal to search for a vacant channel, and the wireless terminal includes: a channel setting unit that sets a channel to be used for wireless communication with the portable wireless terminal; a trigger receiver unit that receives a trigger sent from the portable wireless terminal; a vacant channel search unit that searches for a vacant channel according to the received trigger and sends a signal for changing the set channel to the channel setting unit based on a search result; and a transmitter unit that transmits a signal for reporting the changing to the portable wireless terminal.

The channel setting unit may set the channel before a signal sent from the portable wireless terminal is received.

While the wireless communication with the portable wireless terminal using the channel is being performed, the vacant channel search unit may send the signal for changing the channel to the channel setting unit.

A wireless communication method in a wireless communication system in which a portable wireless terminal and a wireless terminal perform autonomous distributed wireless communication, the wireless communication method including: a sending step in which a transmitter unit of the portable wireless terminal sends a trigger to the wireless terminal, the trigger being used for allowing the wireless terminal to search for a vacant channel; a channel setting step in which a channel setting unit of the wireless terminal sets a channel that is used for performing wireless communication with the portable wireless terminal; a trigger reception step in which a trigger receiver unit of the wireless terminal receives a trigger from the portable wireless terminal; a vacant channel search step in which a vacant channel search unit of the wireless terminal searches for a vacant channel according to the received trigger and sends a signal for changing the set channel to the channel setting unit based on a search result; and a transmission step in which a transmitter unit of the wireless terminal transmits a signal for reporting the changing to the portable wireless terminal.

The channel may be set before a signal sent from the portable wireless terminal is received.

The signal for changing the set channel may be sent while the wireless communication is being performed with the portable wireless terminal by using the channel.

After a channel to be used for communication between wireless terminals is set, when a trigger is received, the wireless terminal of the present invention searches for vacant channels, changes the set channel based on a search result, and sends a signal for reporting a change in the channel to another wireless terminal. Consequently, even after the channel to be used for communication between the wireless terminals is set, it is possible to change the channel to be used for communication between the wireless terminals.

DETAILED DESCRIPTION OF THE PREFERRED EMBODIMENTS

First Preferred Embodiment

Hereinafter, an autonomous distributed wireless communication system in accordance with a first preferred embodiment of the present invention will be described with reference to the accompanying drawings. In addition, the preferred embodiment will be described using a wireless endoscope system. However, the present invention is not limited thereto. For example, the present invention can be applied to an autonomous distributed wireless communication system (for example, a wireless communication system using a wireless local area network (LAN), ZigBee (a registered trademark), Bluetooth (a registered trademark), millimeter-wave radio, body area radio and the like).

Figure 1:
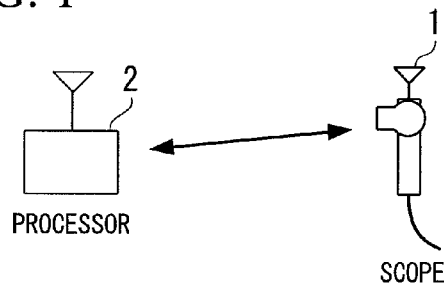
FIG. 1 is a schematic diagram illustrating the configuration of a wireless endoscope system in accordance with a first preferred embodiment of the present invention.

FIG. 1 is a schematic diagram illustrating the configuration of a wireless endoscope system (a wireless communication system) in accordance with the first preferred embodiment of the present invention. In the example illustrated in FIG. 1, the wireless endoscope system includes an endoscope scope 1 (a portable wireless terminal) and a processor 2 (a wireless terminal, a process apparatus).

The endoscope scope 1 and the processor 2 are connected to each other in a communicable state through autonomous distributed wireless communication in which communication is performed without using a base station, an access point or the like. The endoscope scope 1 is inserted into a body cavity of a patient to photograph an image of an inside of the body cavity, and transmits the photographed image to the processor 2 in a wireless manner. The processor 2 receives the image transmitted from the endoscope scope 1 and displays the received image on a monitor.

Figure 2:
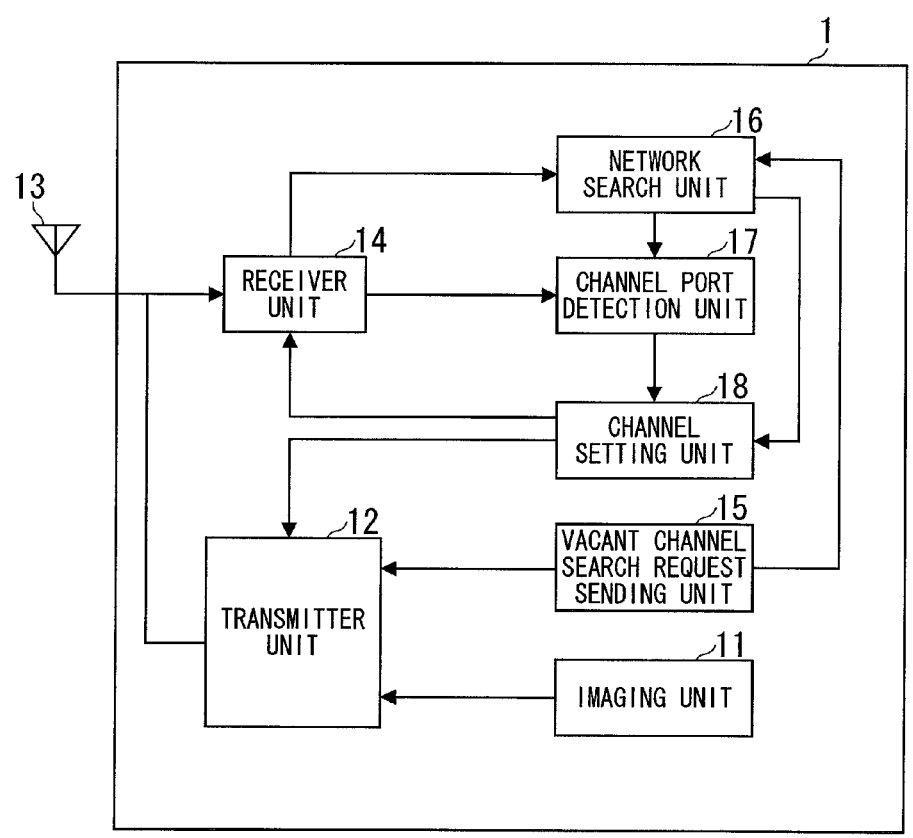
FIG. 2 is a block diagram illustrating the configuration of the endoscope scope in accordance with the first preferred embodiment of the present invention.

Next, the configuration of the endoscope scope 1 will be described. FIG. 2 is a block diagram illustrating the configuration of the endoscope scope 1 in accordance with the first preferred embodiment of the present invention. In the example illustrated in FIG. 2, the endoscope scope 1 includes an image capturing unit 11, a transmitter unit 12, an antenna 13, a receiver unit 14, a vacant channel search request sending unit 15, a network search unit 16, a channel port detection unit 17, and a channel setting unit 18.

The image capturing unit 11 photographs a body cavity to acquire an image, and performs analog/digital conversion and the like with respect to acquired image data. The transmitter unit 12 modulates and transmits a radio signal. The antenna 13 transmits and receives a radio wave. The receiver unit 14 receives and demodulates a radio signal. The vacant channel search request sending unit 15 detects a vacant channel search request (a trigger). The network search unit 16 searches for the processor 2 serving as a connection destination. The channel port detection unit 17 acquires a vacant channel search result included in a channel port received from the processor 2. The channel setting unit 18 sets a channel to be used for the transmission/reception of a radio signal in the transmitter unit 12 and the receiver unit 14.

Next, an operation of the endoscope scope 1 after being activated will be described. After the endoscope scope 1 is powered on, the vacant channel search request sending unit 15 notifies the transmitter unit 12 and the network search unit 16 of the vacant channel search request.

After the network search unit 16 has been notified of the vacant channel search request, the network search unit 16 searches for the processor 2 serving as a connection destination. In detail, the network search unit 16 searches for a channel opened by the processor 2 based on a beacon message transmitted regularly after the processor 2 opens and notifies the channel setting unit 18 of information indicating the channel opened by the processor 2.

After the network search unit 16 has been notified of the information indicating the channel opened by the processor 2, the channel setting unit 18 sets a channel to be used for transmission/reception of a radio signal in the transmitter unit 12 and the receiver unit 14 based on the notified information.

The transmitter unit 12 modulates the vacant channel search request that has been notified of by the vacant channel search request sending unit 15, and transmits the vacant channel search request to the processor 2 using the channel set by the channel setting unit 18 through the antenna 13. Then, the endoscope scope 1 enters a standby state until the channel port transmitted from the processor 2 is received.

Next, the operation of the endoscope scope 1 when the channel port has been transmitted from the processor 2 will be described. The receiver unit 14 hands over the channel port received through the antenna 13 to the channel port detection unit 17. The channel port detection unit 17 acquires a vacant channel search result included in the channel port, and hands over the vacant channel search result to the channel setting unit 18. The channel setting unit 18 sets a channel instructed by the vacant channel search result in the transmitter unit 12 and the receiver unit 14. A vacant channel will be described later.

Through the above-mentioned operation, after the channel is set in the transmitter unit 12 and the receiver unit 15 of the endoscope scope 1, the transmitter unit 12 and the receiver unit 15 of the endoscope scope 1 communicate with the processor 2 using the set channel, and transmit the image data photographed and modulated by the image capturing unit 11 to the processor 2.

Figure 3:
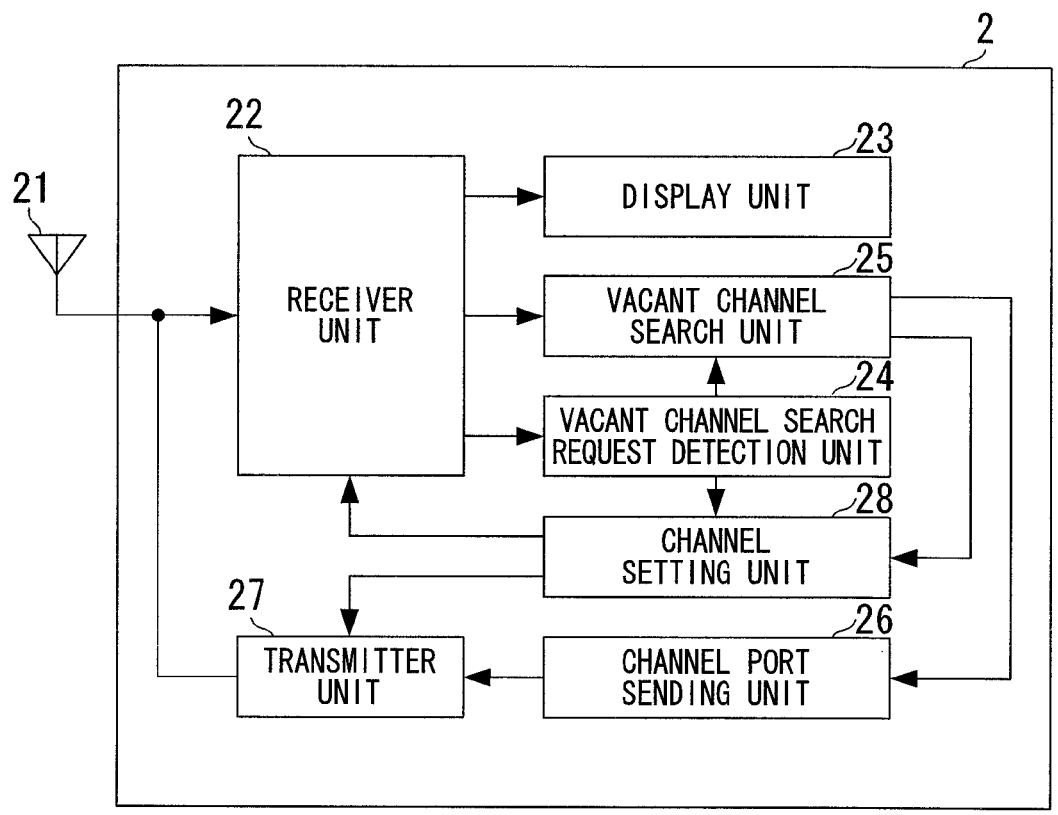
FIG. 3 is a block diagram illustrating the configuration of the processor in accordance with the first preferred embodiment of the present invention.

Next, the configuration of the processor 2 will be described. FIG. 3 is a block diagram illustrating the configuration of the processor 2 in accordance with the first preferred embodiment of the present invention. In the example illustrated in FIG. 3, the processor 2 includes an antenna 21, a receiver unit 22, a display unit 23, a vacant channel search request detection unit 24 (a trigger receiver unit), a vacant channel search unit 25, a channel port sending unit 26, a transmitter unit 27, and a channel setting unit 28.

The antenna 21 transmits and receives a radio wave. The receiver unit 22 receives and demodulates a radio signal. The display unit 23 performs signal processing with respect to the image data transmitted from the endoscope scope 1, and outputs resultant data to the monitor. The vacant channel search request detection unit 24 acquires the vacant channel search request (the trigger) transmitted from the endoscope scope 2. The vacant channel search unit 25 searches for channels, which are vacant channels not used by another apparatus. The channel port sending unit 26 modulates a channel port including a vacant channel search result and sends the channel port to the scope. The transmitter unit 27 modulates and transmits a radio signal. The channel setting unit 28 sets a channel to be used for transmission/reception of a radio signal in the receiver unit 22 and the transmitter unit 27.

Next, an operation of the processor 2 after being activated will be described. After the processor is powered on, the vacant channel search unit 25 searches for channels, which are vacant channels not used by another apparatus, through the antenna 21 and the receiver unit 22. In addition, when a plurality of vacant channels have been detected, the vacant channel search unit 25 selects a channel with the best communication quality from the detected vacant channels. Next, the vacant channel search unit 25 notifies the channel setting unit 28 of vacant channel information which is a vacant channel search result. The channel setting unit 28 sets a channel to be used when the transmitter unit 27 and the receiver unit 22 of the processor transmit and receive a radio signal based on the notified vacant channel information.

In this way, the processor 2 opens. Then, the processor 2 regularly transmits a beacon including information on a channel to be used for communication, and enters a standby state until the vacant channel search request transmitted from the endoscope scope 1 is received. In addition, in relation to the vacant channel search performed by the vacant channel search unit 25, the vacant channel may be selected based on interference power measured in each channel, or the vacant channel may be selected based on a result obtained by measuring the number of wireless communication devices performing communication using each channel or the number of packets.

Next, the operation of the processor 2 when the vacant channel search request has been transmitted from the endoscope scope 1 will be described. If the vacant channel search request transmitted from the endoscope scope 1 is received through the antenna 21 and the receiver unit, the vacant channel search request detection unit 24 gives a vacant channel search instruction to the vacant channel search unit 25.

After the vacant channel search instruction is received, the vacant channel search unit 25 searches for channels which are vacant channels not used by another apparatus. In addition, when a plurality of vacant channels have been detected, the vacant channel search unit 25 selects a channel with the best communication quality from the detected channels. Next, the vacant channel search unit 25 hands over a channel port including information on the vacant channel to the channel port sending unit 26, and gives a channel change instruction to the channel setting unit 28 such that the channel used by the receiver unit 22 and the transmitter unit 27 is changed to the vacant channel (or the channel with the best communication quality among the vacant channels).

The channel port sending unit 26 sends the channel port to the endoscope scope 1 through the transmitter unit 27 and the antenna 21. At this time, the transmitter unit 27 performs a modulation process and a transmission process.

After the channel port sending unit 26 sends the channel port, the channel setting unit 28 sets the vacant channel (or the channel with the best communication quality among the vacant channels) in the transmitter unit 27 and the receiver unit 22 based on the channel change instruction received from the vacant channel search unit 25.

Through the above-mentioned operation, after the channel is set in the transmitter unit 27 and the receiver unit 22 of the processor 2, the transmitter unit 27 and the receiver unit 22 of the processor 2 communicate with the endoscope scope 1 using the set channel, and receive the image data transmitted from the endoscope scope 1. Then, the display unit 23 of the processor 2 performs signal processing with respect to the received image data and outputs resultant data to the monitor.

Figure 4:
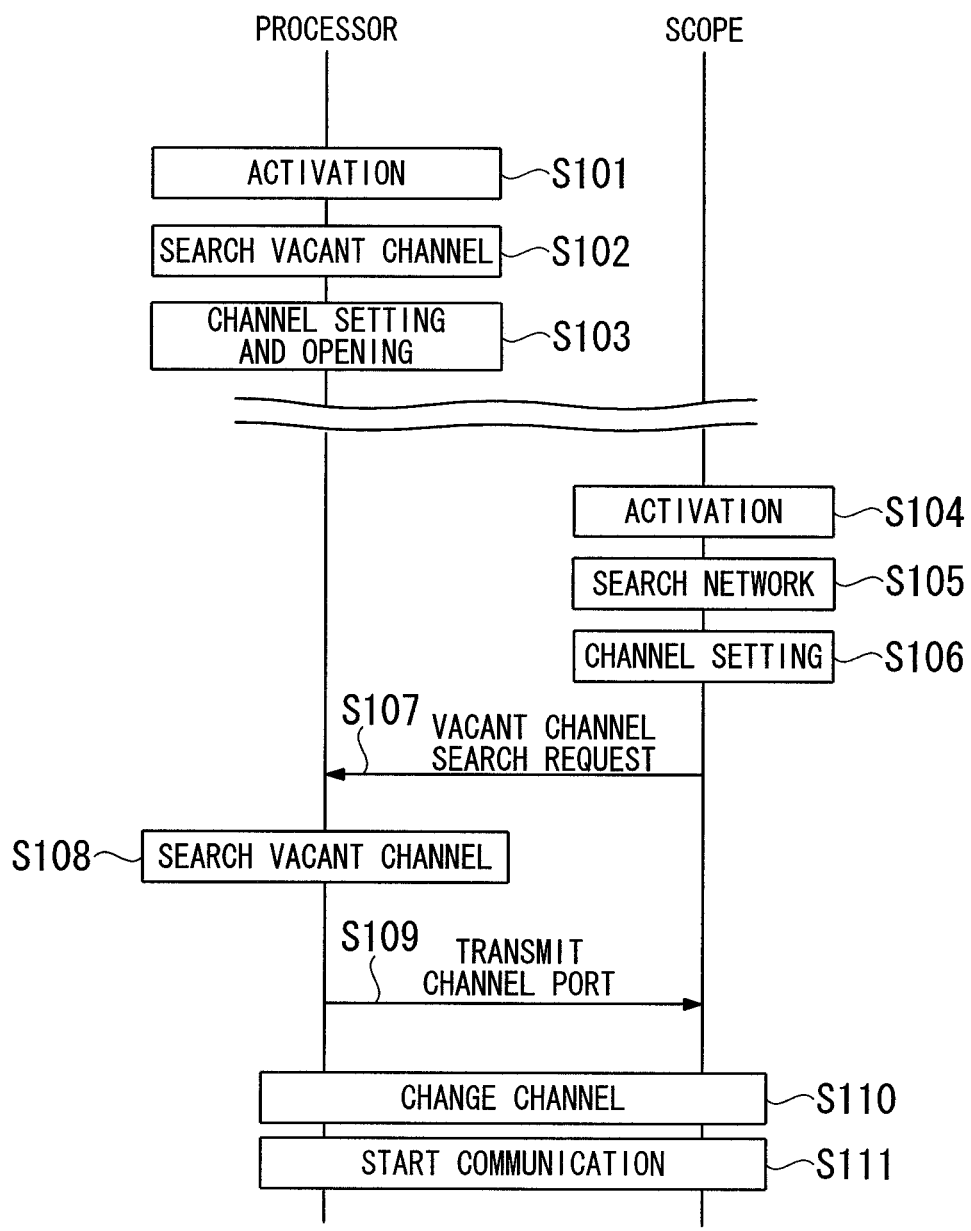
FIG. 4 is a sequence diagram illustrating the process flows of the endoscope scope and the processor in accordance with the first preferred embodiment of the present invention.

Next, the process flows of the endoscope scope 1 and the processor 2 in accordance with the first preferred embodiment will be described with reference to FIG. 4. FIG. 4 is a sequence diagram illustrating the process flows of the endoscope scope 1 and the processor 2 in accordance with the first preferred embodiment of the present invention.

In the example illustrated in FIG. 4, the processor 2 is activated (step S101), performs a vacant channel search (step S102), and opens by setting a channel to be used for communication with the endoscope scope 1 based on a search result (step S103). Then, the processor 2 enters a standby state until the vacant channel search request transmitted from the endoscope scope 1 is received.

After the processor 2 enters the standby state, the endoscope scope 1 is activated (step S104), performs a network search (step S105), and specifies the processor 2 serving as a connection destination and a channel to be used for communication with the processor 2 based on the beacon message regularly transmitted from the processor 2. Next, the endoscope scope 1 sets the channel to be used for communication with the processor 2 serving as the connection destination (step S106), and sends a vacant channel search request to the processor 2 serving as the connection destination (step S107). Then, the endoscope scope 1 enters a standby state until the channel port transmitted from the processor 2 is received.

After the vacant channel search request is received, the processor 2 performs the vacant channel search again (step S108), and specifies a vacant channel. That is, the processor 2 reviews the channel selection. Next, the processor 2 transmits a channel port including information indicating the vacant channel to the endoscope scope 1 (step S109), and then changes the channel used for communication with the endoscope scope 1 to the vacant channel (or the channel with the best communication quality among the vacant channels) (step S110). Meanwhile, after the channel port is received, the endoscope scope 1 also changes the channel used for communication with the processor 2 to the vacant channel (or the channel with the best communication quality among the vacant channels) based on the received channel port (step S110).

In this way, after the channel to be used between the endoscope scope 1 and the processor 2 is set, the endoscope scope 1 and the processor 2 start to communicate with each other (step S111).

Figure 5:
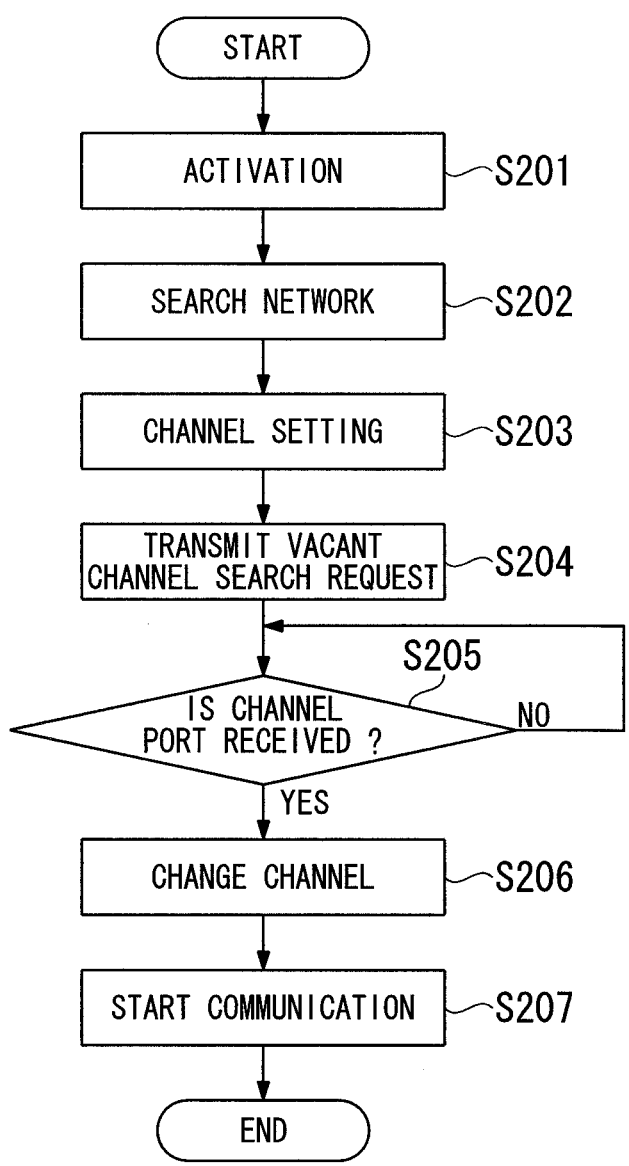
FIG. 5 is a flowchart illustrating the operation procedure of the endoscope scope in accordance with the first preferred embodiment of the present invention.

Next, the operation procedure of the endoscope scope 1 in accordance with the first preferred embodiment will be described. FIG. 5 is a flowchart illustrating the operation procedure of the endoscope scope 1 in accordance with the first preferred embodiment of the present invention.
(Step S201)
The endoscope scope 1 is activated. Then, the procedure proceeds to the process of step S202.
(Step S202)
The network search unit 16 performs network search, and specifies the processor 2 serving as a connection destination and a channel to be used for communication with the processor 2 based on the beacon message regularly transmitted from the processor 2. Then, the procedure proceeds to the process of step S203.
(Step S203)
The channel setting unit 18 sets the channel to be used for communication with the processor 2 serving as the connection destination specified in step S202. Then, the procedure proceeds to the process of step S204.
(Step S204)
The vacant channel search request sending unit 15 sends a vacant channel search request to the processor 2 serving as the connection destination determined in step S202 using the channel set in the process of step S203. Then, the procedure proceeds to the process of step S205.
(Step S205)
If the channel port detection unit 17 receives the channel port from the processor 2, the channel port detection unit 17 proceeds to the process of step S206. Otherwise, the channel port detection unit 17 performs the process of step S205 again. That is, the channel port detection unit 17 waits until the channel port is received.
(Step S206)
The channel setting unit 18 sets the vacant channel (or the channel with the best communication quality among the vacant channels) included in the channel port in the transmitter unit 12 and the receiver unit 14. Then, the procedure proceeds to the process of step S207.
(Step S207)
The endoscope scope 1 starts to communicate with the processor 2.

Figure 6:
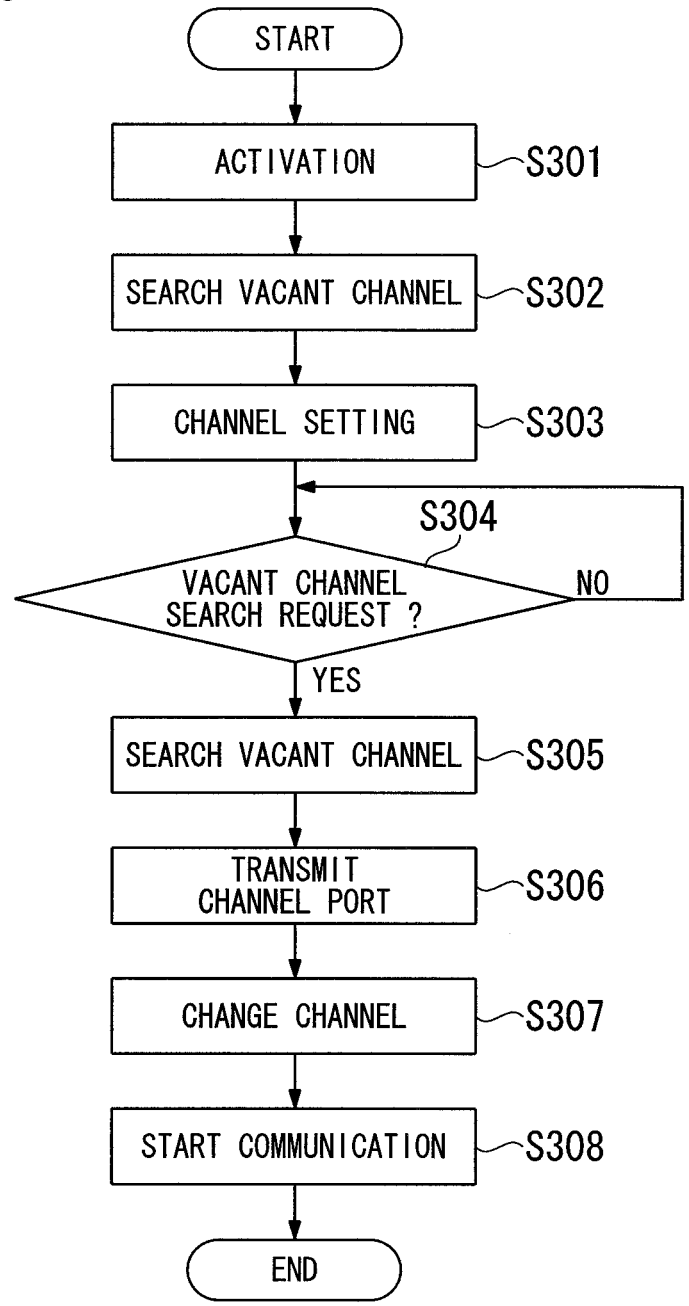
FIG. 6 is a flowchart illustrating the operation procedure of the processor in accordance with the first preferred embodiment of the present invention.

Next, the operation procedure of the processor 2 in accordance with the first preferred embodiment will be described. FIG. 6 is a flowchart illustrating the operation procedure of the processor 2 in accordance with the first preferred embodiment of the present invention.
(Step S301)
The processor 2 is activated. Then, the procedure proceeds to the process of step S302.
(Step S302)
The vacant channel search unit 25 performs a vacant channel search and specifies the vacant channel (or the channel with the best communication quality among the vacant channels). Then, the procedure proceeds to the process of step S303.
(Step S303)
The channel setting unit 28 sets the vacant channel (or the channel with the best communication quality among the vacant channels) specified in step S302 in the transmitter unit 27 and the receiver unit 22. In this way, the processor 2 opens. Then, the procedure proceeds to the process of step S304.
(Step S304)
If the vacant channel search request detection unit 24 receives the vacant channel search request from the endoscope scope 1, the vacant channel search request detection unit 24 proceeds to the process of step S305. Otherwise, the vacant channel search request detection unit 24 performs the process of step S304. That is, the vacant channel search request detection unit 24 waits until the vacant channel search request is received.
(Step S305)
The vacant channel search unit 25 performs a vacant channel search and specifies a vacant channel. In addition, when a plurality of vacant channels have been detected, the vacant channel search unit 25 selects a channel with the best communication state. Furthermore, the vacant channel search unit 25 hands over the channel port including the information on the vacant channel to the channel port sending unit 26. Then, the procedure proceeds to the process of step S306.
(Step S306)
The channel port sending unit 26 sends the channel port to the endoscope scope 1. Then, the procedure proceeds to the process of step S307.
(Step S307)
The channel setting unit 18 sets the vacant channel (or the channel with the best communication quality among the vacant channels) detected by the vacant channel search unit 25 in step S305 in the transmitter unit 12 and the receiver unit 14. Then, the procedure proceeds to the process of step S308.

(Step S308)

The processor 2 starts to communicate with the endoscope scope 1.

As described above, the processor 2 of the first preferred embodiment is activated and then sets the channel to be used for communication with the endoscope scope 1. Furthermore, the endoscope scope 1 is activated and then transmits the vacant channel search request to the processor 2. Furthermore, after the vacant channel search request is received, the processor 2 searches vacant channels, sets a channel again to be used for communication with the endoscope scope 1 based on a search result, and transmits a channel port including information on a changed channel to the endoscope scope 1. Furthermore, the endoscope scope 1 sets a channel to be used for communication with the processor 2 based on the channel port.

In this way, after the processor 2 is activated, even when a wireless communication environment is changed by the time the endoscope scope 1 is activated, the processor 2 searches for vacant channels again at a timing appropriate for a user, for example, at the time of communication start or power-on of the scope. Consequently, it is possible for the processor 2 to assign a channel optimal for communication, so that the endoscope scope 1 and the processor 2 can communicate with each other using the optimal channel.

Second Preferred Embodiment

Hereinafter, a second preferred embodiment of the present invention will be described with reference to the accompanying drawings. In addition, the configuration of a processor 2 in accordance with the second preferred embodiment is similar to that of the processor 2 in accordance with the first preferred embodiment.

Figure 7:
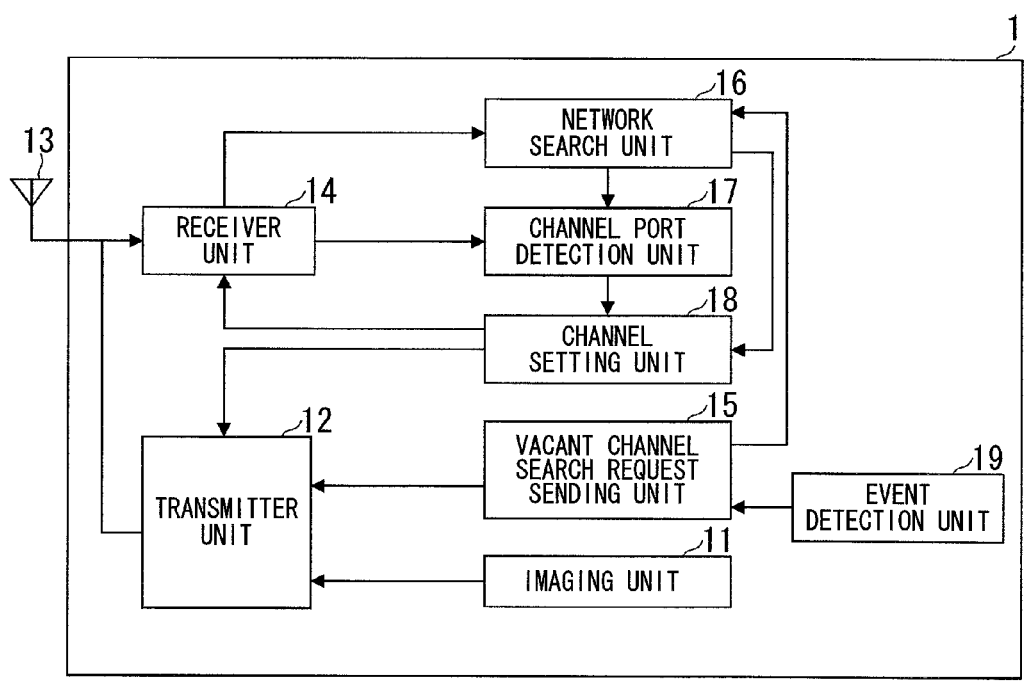
FIG. 7 is a block diagram illustrating the configuration of an endoscope scope in accordance with a second preferred embodiment of the present invention.

Next, the configuration of an endoscope scope 1 in accordance with the second preferred embodiment will be described. FIG. 7 is a block diagram illustrating the configuration of an endoscope scope 1 in accordance with the second preferred embodiment of the present invention. The configuration of the endoscope scope 1 in accordance with the second preferred embodiment is substantially identical to the configuration of the endoscope scope 1 in accordance with the first preferred embodiment, except that the endoscope scope 1 in accordance with the second preferred embodiment includes an event detection unit 19.

In the example illustrated in FIG. 7, the endoscope scope 1 includes an image capturing unit 11, a transmitter unit 12, an antenna 13, a receiver unit 14, a vacant channel search request sending unit 15, a network search unit 16, a channel port detection unit 17, a channel setting unit 18, and the event detection unit 19. In addition, the image capturing unit 11, the transmitter unit 12, the antenna 13, the receiver unit 14, the vacant channel search request sending unit 15, the network search unit 16, the channel port detection unit 17, and the channel setting unit 18 in accordance with the second preferred embodiment are identical to those in accordance with the first preferred embodiment.

The event detection unit 19 detects an event for starting diagnosis occurring in the endoscope scope 1, and notifies the vacant channel search request sending unit 15 of information indicating the detection of the event for starting diagnosis. After the information indicating the detection of the event for starting diagnosis has been notified of, the vacant channel search request sending unit 15 transmits a vacant channel search request to the processor 2 through the transmitter unit 12 and the antenna 13.

In addition, the event for starting diagnosis corresponds to a process which is performed before starting diagnosis. For example, in relation to the detection of the event for starting diagnosis, switch pressing of white balance adjustment of an image necessarily performed before diagnosis may be detected, the pressing of a dedicated switch for setting a channel again by a surgical operator may be detected, a result obtained by detecting gripping of the endoscope by an operator by using a switch or a sensor, or input of patient information for starting diagnosis may be detected. Furthermore, it may be possible to acquire location information using GPS and the like to detect entrance to a diagnosis room, to detect that the distance between the processor 2 and the endoscope scope 1 is less than or equal to a constant value using a laser or a communication device with a short communication distance, or to detect that a constant time has passed since the endoscope scope 1 was powered on.

Figure 8:
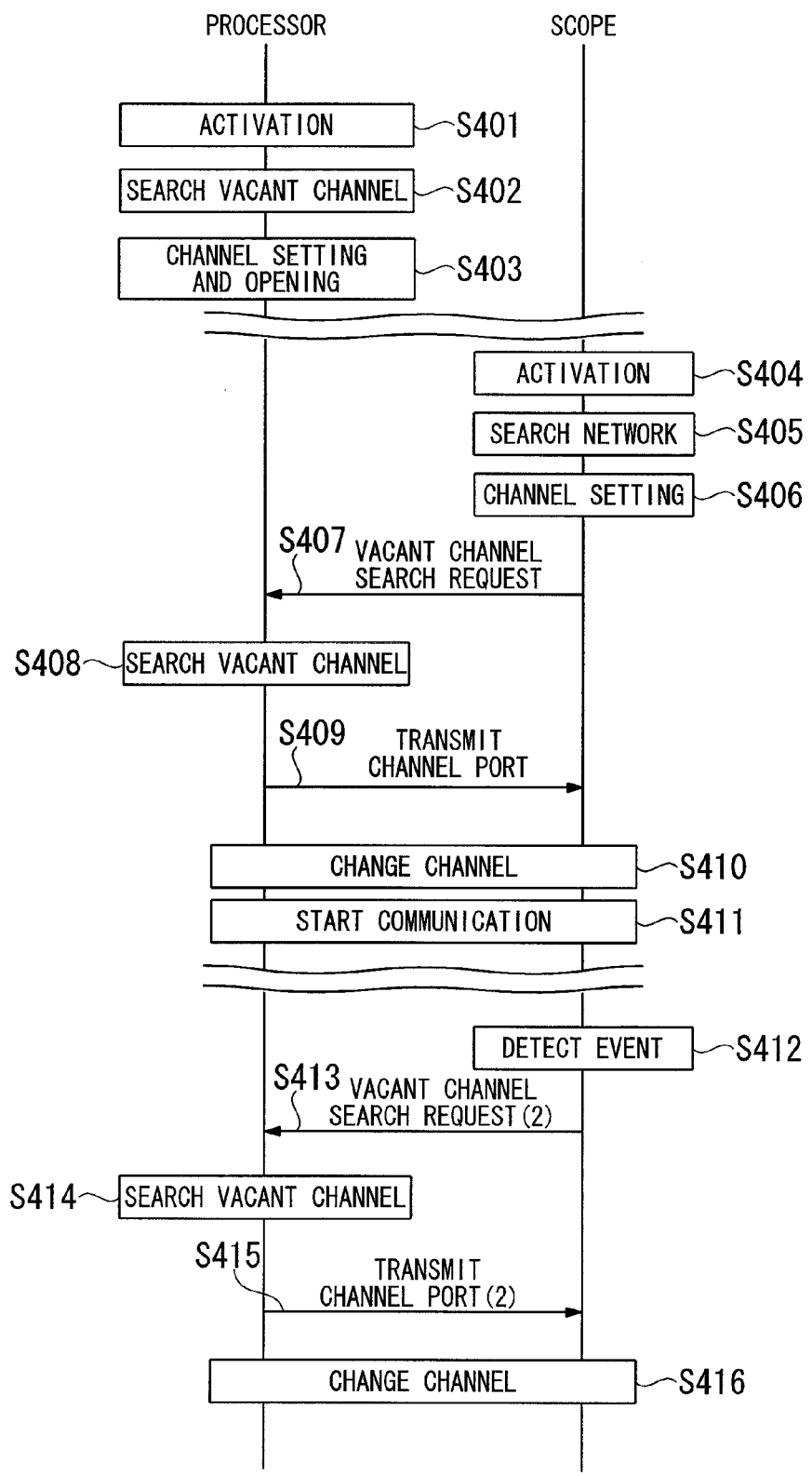
FIG. 8 is a sequence diagram illustrating the process flows of the endoscope scope and the processor in accordance with the second preferred embodiment of the present invention.

Next, the process flows of the endoscope scope 1 and the processor 2 in accordance with the second preferred embodiment will be described with reference to FIG. 8. FIG. 8 is a sequence diagram illustrating the process flows of the endoscope scope 1 and the processor 2 in accordance with the second preferred embodiment of the present invention.

Hereinafter, since the processes of step S401 to step S411 in accordance with the second preferred embodiment are identical to the processes of step S101 to step S111 in accordance with the first preferred embodiment, description thereof will be omitted.

In the example illustrated in FIG. 8, since processes after the endoscope scope 1 and the processor 2 start to communicate with each other, that is, processes after step S412, are added, the processes after step S412 will be sequentially described.

After starting to communicate with the processor 2, when the event detection unit 19 has detected an event for starting diagnosis (step S412), the endoscope scope 1 sends a vacant channel search request to the processor 2 (step S413).

After the vacant channel search is received, the processor 2 performs a vacant channel search again (step S414) and specifies a vacant channel. In addition, when a plurality of vacant channels have been detected, the vacant channel search unit 25 selects a channel with the best communication quality. That is, the processor 2 reviews channel selection.

Next, the processor 2 transmits a channel port including information indicating the vacant channel to the endoscope scope 1 (step S415), and then changes a channel used for communicating with the endoscope scope 1 to the vacant channel (or the channel with the best communication quality among the vacant channels) (step S416). Meanwhile, after the channel port is received, the endoscope scope 1 also changes a channel used for communicating with the processor 2 to the vacant channel (or the channel with the best communication quality among the vacant channels) based on the received channel port (step S416).

Figure 9:
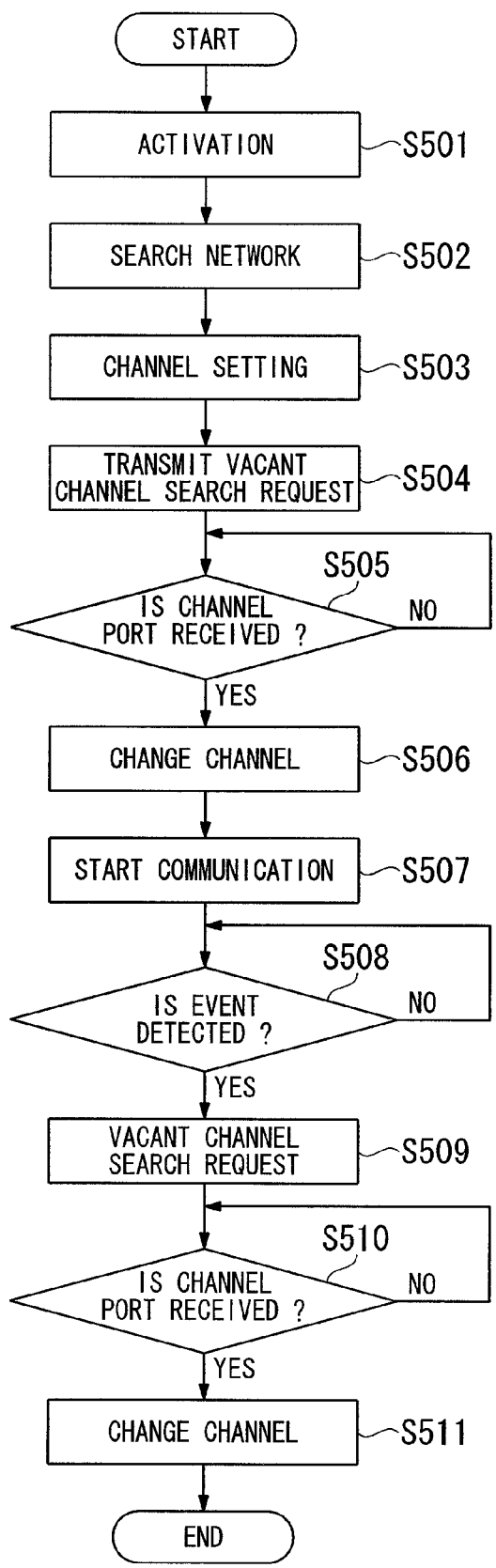
FIG. 9 is a flowchart illustrating the operation procedure of the endoscope scope in accordance with the second preferred embodiment of the present invention.

Next, the operation procedure of the endoscope scope 1 in accordance with the second preferred embodiment will be described. FIG. 9 is a flowchart illustrating the operation procedure of the endoscope scope 1 in accordance with the second preferred embodiment of the present invention.

Hereinafter, since the processes of step S501 to step S507 in accordance with the second preferred embodiment are identical to the processes of step S201 to step S207 in accordance with the first preferred embodiment, description thereof will be omitted.

In the example illustrated in FIG. 9, since processes after the endoscope scope 1 and the processor 2 start to communicate with each other, that is, processes after step S508, are added, the processes after step S508 will be sequentially described.

(Step S508)

While the endoscope scope 1 and the processor 2 are communicating with each other, if the event detection unit 19 has detected an event for starting diagnosis, the event detection unit 19 proceeds to the process of step S509. Otherwise, the event detection unit 19 performs the process of step S508 again. That is, the endoscope scope 1 waits until the event detection unit 19 detects the event for starting diagnosis.

(Step S509)

The vacant channel search request sending unit 15 sends a vacant channel search request to the processor 2. Then, the procedure proceeds to the process of step S510.

(Step S510)

If the channel port detection unit 17 receives the channel port from the processor 2, the channel port detection unit 17 proceeds to the process of step S511. Otherwise, the channel port detection unit 17 performs the process of step S510 again. That is, the channel port detection unit 17 waits until the channel port is received.

(Step S511)

The channel setting unit 18 sets the vacant channel (or the channel with the best communication quality among the vacant channels) included in the channel port in the transmitter unit 12 and the receiver unit 14.

Figure 10:
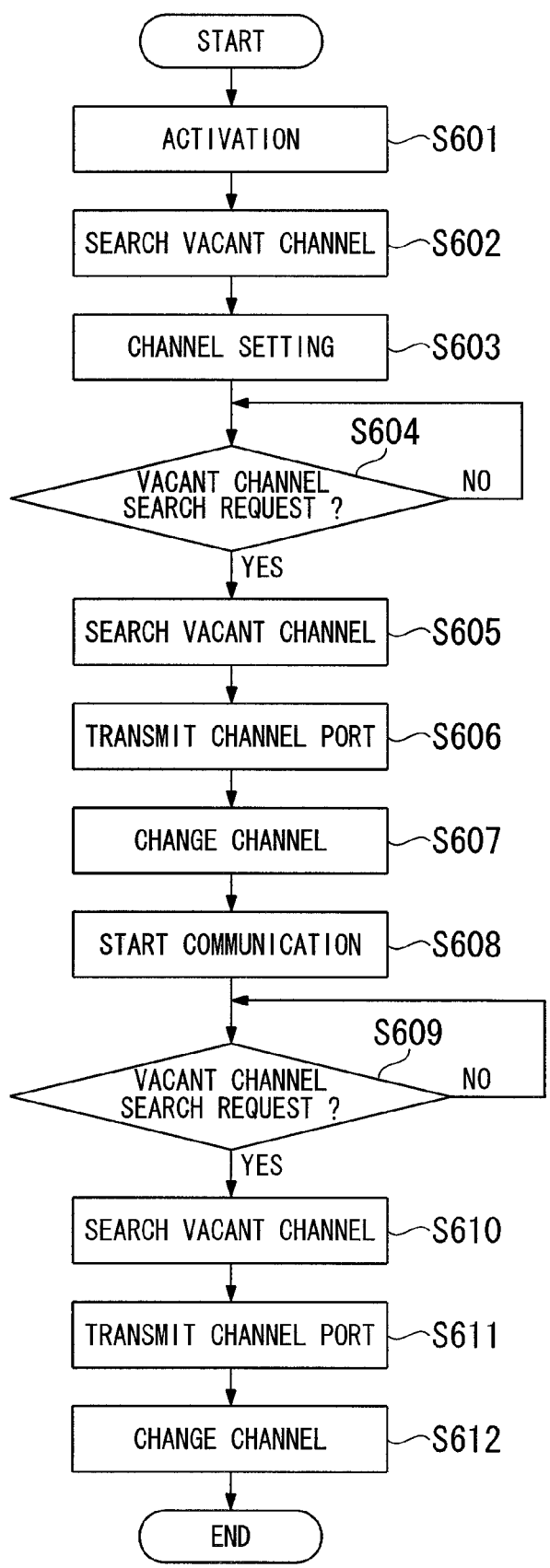
FIG. 10 is a flowchart illustrating the operation procedure of the processor in accordance with the second preferred embodiment of the present invention.

Next, the operation procedure of the processor 2 in accordance with the second preferred embodiment will be described. FIG. 10 is a flowchart illustrating the operation procedure of the processor 2 in accordance with the second preferred embodiment of the present invention.

Hereinafter, since the processes of step S601 to step S608 in accordance with the second preferred embodiment are identical to the processes of step S301 to step S308 in accordance with the first preferred embodiment, description thereof will be omitted.

In the example illustrated in FIG. 10, since processes after the processor 2 and the endoscope scope 1 start to communicate with each other, that is, processes after step S609, are added, the processes after step S609 will be sequentially described.

(Step S609)

If the vacant channel search request detection unit 24 receives the vacant channel search request from the endoscope scope 1, the vacant channel search request detection unit 24 proceeds to the process of step S610. Otherwise, the vacant channel search request detection unit 24 performs the process of step S609 again. That is, the vacant channel search request detection unit 24 waits until the vacant channel search request is received.

(Step S610)

The vacant channel search unit 25 performs a vacant channel search and specifies a vacant channel. In addition, when a plurality of vacant channels have been detected, the vacant channel search unit 25 selects a channel with the best communication state. Furthermore, the vacant channel search unit 25 hands over a channel port including information on the vacant channel to the channel port sending unit 26. Then, the procedure proceeds to the process of step S611.

(Step S611)

The channel port sending unit 26 sends the channel port to the endoscope scope 1. Then, the procedure proceeds to the process of step S612.

(Step S612)

The channel setting unit 18 sets the vacant channel (or the channel with the best communication quality among the vacant channels) detected by the vacant channel search unit 25 in step S610 in the transmitter unit 12 and the receiver unit 14.

As described above, before diagnosis actually starts, the endoscope scope 1 in accordance with the second preferred embodiment transmits the vacant channel search request to the processor 2 again. Furthermore, after the vacant channel search request is received, the processor 2 searches vacant channels, sets a channel again to be used for communication with the endoscope scope 1 based on a search result, and transmits a channel port including information on a changed channel to the endoscope scope 1. Furthermore, the endoscope scope 1 sets a channel to be used for communication with the processor 2 based on the channel port.

Consequently, for example, when a surgical operator activates the endoscope scope 1 in a management area and then moves into a diagnosis room with the endoscope scope 1 in his or her hand, it is possible to search for vacant channels again at the time and place where diagnosis actually starts and assign an optical channel, so that the endoscope scope 1 and the processor 2 can communicate with each other using the optical channel.

In addition, in the flowcharts illustrated in FIGS. 9 and 10, the event detection process and the vacant channel search process are performed only once as the processes after communication starts. However, the event detection process and the vacant channel search process may be repeated in a loop twice or more. In detail, in the flowchart illustrated in FIG. 9, the processes from step S508 to step S511 may be repeated. Furthermore, in the flowchart illustrated in FIG. 10, the processes from step S609 to step S612 may be repeated.

While the first and second preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the invention is not to be considered as being limited by the foregoing description, and is only limited by the scope of the claims.

For example, in the first and second preferred embodiments, the wireless endoscope system provided with one endoscope scope 1 has been described as an example. However, the present invention is not limited thereto. For example, the present invention can be applied to a wireless endoscope system provided with a plurality of endoscope scopes 1.

Furthermore, as described above, the endoscope scope 1 and the processor 2 in accordance with the first and second preferred embodiments can avoid interference without a wireless communication unit (for example, an RFID tag reader, an RFID and the like) different from a wireless communication unit for image data transmission. Consequently, it is possible to avoid crosstalk without an apparatus becoming more expensive. That is, as an additional effect, it is possible to avoid crosstalk without an apparatus becoming more expensive.

The wireless terminal of the present invention can set a channel to be used for communication between wireless terminals and then change the channel to be used for communication between the wireless terminals, so that it is possible to perform reliable communication using a plurality of wireless terminals.

What is claimed is:

1. A portable wireless terminal that performs autonomous distributed wireless communication with a wireless terminal, the wireless terminal including a second channel setting unit that sets a channel to be used for wireless communication with the portable wireless terminal, a trigger receiver unit that receives a trigger, a vacant channel search unit that searches for a vacant channel according to the received trigger and sends a signal for changing the set channel to the second channel setting unit based on a search result, and a transmitter unit that transmits a signal for reporting the change to the portable wireless terminal, the portable wireless terminal comprising;
 a trigger sending unit that sends a trigger to the wireless terminal, the trigger being used for allowing the wireless terminal to search for a vacant channel;
 a first channel setting unit that sets a channel to be used for wireless communication with the wireless terminal based on channel information which is a response for the sent trigger from the wireless terminal:
 an event detection unit that detects a predetermined event after wireless communication using the channel that has been set by the first channel setting unit is started,
 wherein the trigger sending unit sends the trigger if the event detection unit detects the predetermined event,
 wherein the event detection unit detects the portable wireless terminal being operated.

2. A portable wireless terminal that performs autonomous distributed wireless communication with a wireless terminal, the wireless terminal including a second channel setting unit that sets a channel to be used for wireless communication with the portable wireless terminal, a trigger receive unit that receives a trigger,
 a vacant channel search unit that searches for a vacant channel according to the received trigger and sends a signal for changing the set channel to the second channel setting unit based on a search result, and a transmitter unit that transmits a signal for reporting the change to the portable wireless terminal, the portable wireless terminal comprising:
 a trigger sending unit that sends a trigger to the wireless terminal, the trigger being used for allowing the wireless terminal to search for a vacant channel;
 a first channel setting unit that sets a channel to be used for wireless communication with the wireless terminal based on channel information which is a response for sent trigger from the wireless terminal;
 an event detection unit that detects a predetermined event after wireless communication using the channel that has been set by the first channel setting unit is started,
 wherein the trigger sending unit sends the trigger if the event detection unit detects the predetermined event,
 wherein the portable wireless terminal is an endoscope scope of a wireless endoscope system,
 the wireless terminal is an endoscope processor of the wireless endoscope system,
 the event detection unit, after wireless communication with the endoscope processor is started, performs at least one of
  detecting pressing of a switch for adjusting white balance,
  detecting gripping of the endoscope scope by an operator, acquiring location information to detect entrance to a diagnosis room,
  detecting a distance with the endoscope processor being less than or equal to a predetermined value,
  detecting that a constant time has passed since the endoscope scope was powered on, and
 as an event for starting a diagnosis, and
 the trigger sending unit sends the trigger to the endoscope processor if the event detection unit detects the event for starting the diagnosis.

3. A portable wireless terminal that performs autonomous distributed wireless communication with a wireless terminal, the wireless terminal including a second channel setting unit that sets a channel to be used for wireless communication with the portable wireless terminal, a trigger receiver unit that receives a trigger, a vacant channel search unit that searches for a vacant channel according to the received trigger and sends a signal for changing the set channel to the second channel setting unit based on a search result, and a transmitter unit that transmits a signal for reporting the channel to the portable wireless terminal, the portable wireless terminal comprising:
 a trigger sending unit that sends a trigger to the wireless terminal, the trigger being used for allowing the wireless terminal to search for a vacant channel;
 a first channel setting unit that sets a channel to be used for wireless communication with the wireless terminal based on channel information which is a response for the sent trigger from the wireless terminal:
 an event detection unit that detects a predetermined event after wireless communication using the channel that has been set by the first channel setting unit is started,
 wherein the trigger sending unit sends the trigger if the event detection unit detects the predetermined event,
 wherein the trigger sending unit sends the trigger after the channel is set in the first channel setting unit,
 the first channel setting unit changes the channel, which has currently been set in the first channel setting unit, based on channel information which is a response for the sent trigger from the wireless terminal.

4. A wireless communication system in which a portable wireless terminal and a wireless terminal perform autonomous distributed wireless communication, wherein
 the portable wireless terminal comprises:
 a trigger sending unit that sends a trigger to the wireless terminal, the trigger being used for allowing the wireless terminal to search for a vacant channel;
 a first channel setting unit that sets a channel to be used for wireless communication with the wireless terminal based on channel information which is a response for the sent trigger from the wireless terminal; and
 an event detection unit that detects a predetermined event after wireless communication using the channel that has been set by the first channel setting unit is started, the trigger sending unit sends the trigger if the event detection unit detects the predetermined event,
 the wireless terminal comprises:
 a second channel setting unit that sets a channel to be used for wireless communication with the portable wireless terminal: a trigger receiver unit that receives a trigger sent from the portable wireless terminal;
 a vacant channel search unit that searches for a vacant channel according to the received trigger, and sends a signal for changing the set channel to the first channel setting unit and the second channel setting unit based on a search result;
 a transmitter unit that opens wireless communication using the channel set in the second channel setting unit and transmits channel information set in the second channel setting unit to the portable wireless terminal,
 wherein the portable wireless terminal is an endoscope scope of a wireless endoscope system,
 the wireless terminal is an endoscope processor of the wireless endoscope system, the event detection unit, after wireless communication with the endoscope processor is started, performs at least one of detecting pressing of a switch for adjusting white balance, detecting gripping of the endoscope scope by an operator, acquiring location information to detect entrance to a diagnosis room, detecting a distance with the endoscope processor being less than or equal to a predetermined value, detecting that a constant time has passed since the endoscope scope was powered on, as an event for starting a diagnosis, and the trigger sending unit sends the trigger to the endoscope processor if the event detection unit detects the event for starting the diagnosis.

5. A wireless communication method in a wireless communication system in which a portable communication, the wireless terminal including:

a channel setting unit that sets a channel to be used for wireless communication with the portable wireless terminal a trigger receiver unit that receives a trigger; a vacant channel search unit that searches for a vacant channel according to the received trigger, and sends a signal for changing the set channel to the second channel setting unit based on a search result; and a transmitter unit that transmits a signal for reporting the change to the portable wireless terminal, the wireless communication method comprising:

a trigger sending step of sending a trigger to the wireless terminal, the trigger being used for allowing the wireless terminal to search for a vacant channel;

a channel setting step, of setting a channel that is used for performing wireless communication with portable wireless terminal based on channel information which is a response for the sent trigger from the wireless terminal;

an event detection step of detecting a predetermined event after wireless communication using the channel that has been set by the first channel setting step is started, wherein, the trigger sending step, the trigger is sent if the predetermined event is detected in the event detection step, wherein the portable wireless terminal is an endoscope scope of a wireless endoscope system, the wireless terminal is an endoscope processor of the wireless endoscope system, in the event detection step, after wireless communication with the endoscope processor is started, at least one of detecting pressing of a switch for adjusting white balance, detecting gripping of the endoscope scope by an operator, acquiring location information to detect entrance to a diagnosis room, detecting a distance with the endoscope processor being less than or equal to a predetermined value, and detecting that a constant time has passed since the endoscope scope was powered on, is performed as an event for starting a diagnosis, and in the trigger sending step, the trigger is sent to the endoscope processor if the event detection unit detects the event for starting the diagnosis.

* * * * *